United States Patent [19]
Trott et al.

[11] Patent Number: 6,074,395
[45] Date of Patent: Jun. 13, 2000

[54] CANNULATED TISSUE ANCHOR INSERTION SYSTEM

[75] Inventors: A. Frank Trott, Largo; Sam R. Marchand, Dunedin, both of Fla.; Anne F. Booth, Barrington, Ill.

[73] Assignee: Linvatec Corporation, Largo, Fla.

[21] Appl. No.: 09/243,059

[22] Filed: Feb. 2, 1999

[51] Int. Cl.$^7$ ................................................. A61B 17/88
[52] U.S. Cl. .............................. 606/104; 606/75; 606/139
[58] Field of Search ................................. 606/72, 73, 75, 606/99, 104, 139, 142, 1

[56] References Cited

U.S. PATENT DOCUMENTS

| | | |
|---|---|---|
| 204,913 | 6/1878 | Pratt . |
| 2,065,659 | 12/1936 | Cullen . |
| 2,243,717 | 5/1941 | Moreira . |
| 2,248,054 | 7/1941 | Becker . |
| 2,267,925 | 12/1941 | Johnston . |
| 2,413,142 | 12/1946 | Jones et al. . |
| 2,631,584 | 3/1953 | Purificato . |
| 2,725,053 | 11/1955 | Bambara et al. . |
| 3,399,432 | 9/1968 | Merser . |
| 3,470,834 | 10/1969 | Bone . |
| 3,716,058 | 2/1973 | Tanner, Jr. . |
| 3,892,232 | 7/1975 | Neufeld . |
| 4,263,903 | 4/1981 | Griggs . |
| 4,462,395 | 7/1984 | Johnson . |
| 4,493,323 | 1/1985 | Albright et al. . |
| 4,884,572 | 12/1989 | Bays et al. . |
| 4,895,148 | 1/1990 | Bays et al. ............................. 606/213 |
| 4,924,865 | 5/1990 | Bays et al. ............................. 606/77 |
| 4,976,715 | 12/1990 | Bays et al. ............................. 606/77 |
| 5,569,252 | 10/1996 | Justin et al. ............................ 606/73 |
| 5,730,744 | 3/1998 | Justin et al. ............................ 606/73 |
| 5,928,252 | 7/1999 | Steadman et al. . |

FOREIGN PATENT DOCUMENTS

| | | |
|---|---|---|
| 0 770 354 | 10/1996 | European Pat. Off. . |
| 196243 | 11/1964 | Russian Federation . |

OTHER PUBLICATIONS

Linvatec Product Brochure, "Is Soft Bone Too Hard For Your Anchor?" Introducing Ultrafix RC Rotatator Cuff Suture Anchor System, 1997, Two Pages.

Linvatec Product Brochure, "Ultrafix RC Suture Anchor System", 1997, Two Pages.

*Primary Examiner*—Michael Buiz
*Assistant Examiner*—David O. Reip
*Attorney, Agent, or Firm*—Gene Warzecha

[57] ABSTRACT

A system for inserting a cannulated tissue anchor during endoscopic or other surgical procedures. The system incorporates an insertion instrument for inserting into a surgical site of implantation an elongated generally cylindrical tissue anchor having, for example, a plurality of barbs outwardly extending from its body and a transverse head situated at its proximal end. The anchor may be inserted by a single-handed operation of the instrument through a series of sequential pulls of a trigger, each pull affecting motion of a particular element. In a preferred embodiment, three trigger pulls are sufficient to penetrate the site of implantation and deliver the anchor slidably along the needle. The instrument operates with replaceable subassemblies each containing a particular size cannulated anchor, having a longitudinally slidable needle for guiding the anchor into place and a longitudinally slidable push rod for pushing the anchor along the needle.

35 Claims, 13 Drawing Sheets

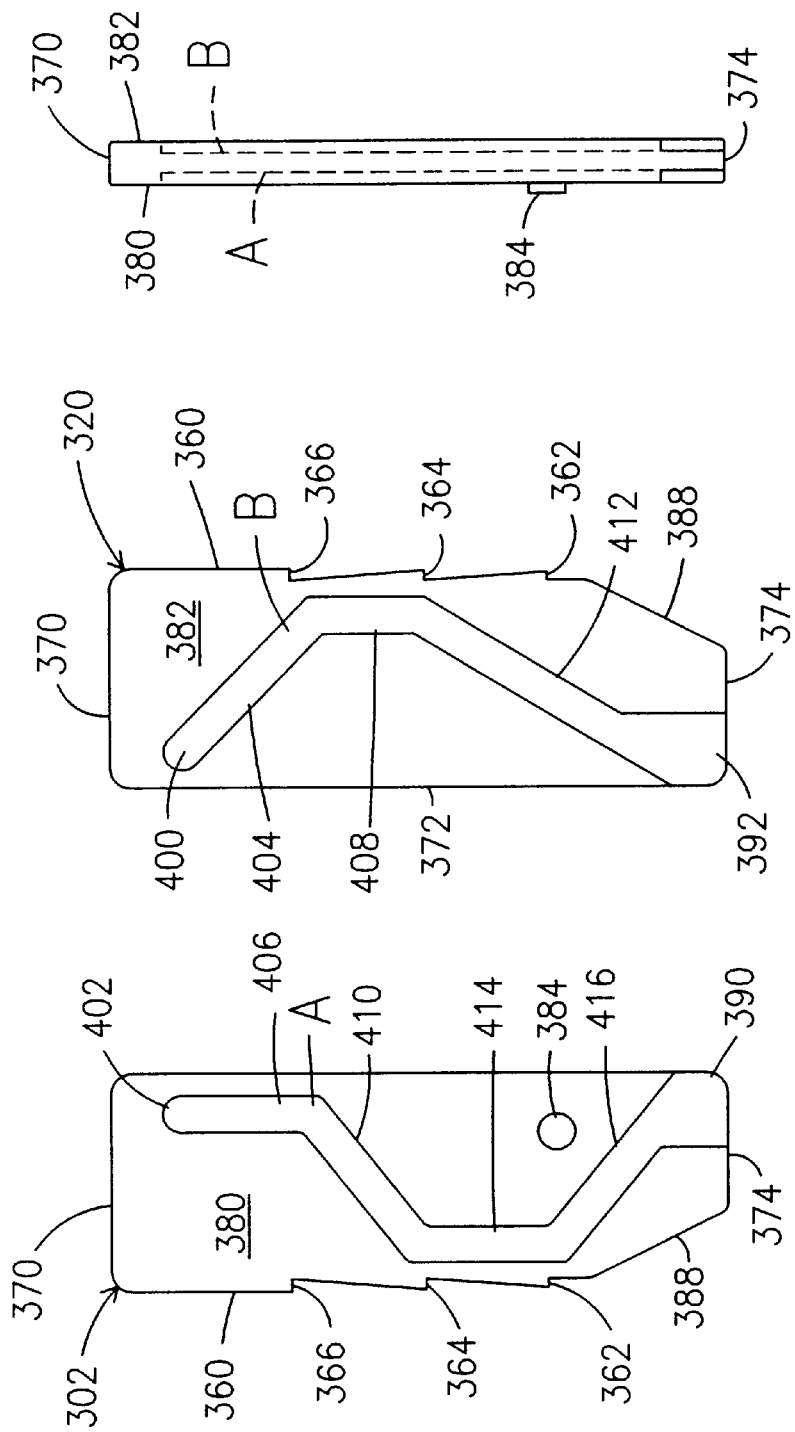

6,074,395

CANNULATED TISSUE ANCHOR INSERTION SYSTEM

BACKGROUND OF THE INVENTION

1. Field of the Invention

The invention relates to implant devices and instruments used to repair body tissue. In particular, the invention relates to a implant devices, instruments and methods for repairing body tissue during endoscopic surgical procedures. Still more particularly, the invention relates to implant devices, instruments and methods for repairing meniscal tissue during arthroscopic surgery of the knee.

2. Description of the Prior Art

Implant devices for repairing body tissue are known in the prior art. While such devices may be classified into several categories, the present invention is related to instruments and methods for inserting into a site of implantation elongated devices having transversely extending barbs or projections which assist in retaining the implant in place within a tissue defect (e.g. a tear) to hold body tissue in close approximation for healing or other reasons.

One such known device is described in U.S. Pat. No. 4,873,976 (Schrieber). This device comprises a solid elongated shaft having a plurality of transversely extending projections, a pointed tip and a transverse circular head at its proximal end. The Schrieber device is inserted at a surgical site of implantation by being pushed through an elongated hollow tube which is held next to, but does not itself penetrate the site of implantation.

Other similar devices are disclosed in U.S. Pat. Nos. 4,884,572; 4,895,148; 4,924,865; and 4,976,715 all issued to Bays et al. The devices disclosed in these Bays et al. patents primarily differ from the Schrieber device in that they are cannulated. The Bays et al. patents are assigned to the assignee hereof and, along with the Schrieber patent, are incorporated by reference herein. The Bays et al. device is inserted at a surgical site of implantation with an applicator having a needle passing through an axial bore of the applicator and through an axial bore of the implant. The implant is held at the tip of the applicator and inserted into the site of implantation directly through a portal or through an insertion cannula. The needle protrudes distally from the implant and both the needle and implant are pushed into the tissue while so assembled. The needle is then disassembled from the applicator and removed.

All of the above described elongated devices are arrow-like and are designed to be inserted or pushed into tissue to be repaired. The devices are sometimes referred to as "tissue anchors" because they hold tissue together during healing. While these devices are intended to be used during arthroscopic, or more generally endoscopic procedures, that very fact makes the insertion sometimes difficult. As described above, it is known to use elongated cannulas to guide the implants into position and smaller push rods to push them in. Insertion devices and methods used with the Schrieber type non-cannulated device require the implant to be pushed through a cannula with an elongated pusher sized to be slidingly received within the cannula. Insertion devices and methods used with cannulated devices such as those disclosed in the Bays et al. patents require the implant device to be secured to the distal tip of a holding device and pushed into place, with or without the use of a guiding cannula. An improved cannulated implant and insertion system have been recently developed and are described in pending U.S. patent application Ser. No. 09/141,175 entitled Cannulated Tissue Anchor System, assigned to the assignee hereof and incorporated by reference herein. The insertion system shown in this application comprises a housing, an elongated tubular shaft extending distally from the housing, the shaft having an axially aligned bore therethrough and an elongated needle adapted to be slidably received within the bore of the shaft. The shaft is adapted to receive a cannulated tissue anchor while the needle is adapted to be received in the bore of the anchor. A trigger means is provided on the housing for moving the distal end of the needle between a first, retracted position, in which the needle is maintained within the shaft bore, and a second, extended position, in which the needle is extended distally, beyond the shaft bore. A push rod for pushing the anchor out of the device is adapted to be slidably received within the shaft bore and moved between a first, retracted position, in which the distal end of the push rod is maintained within the shaft bore, and a second, extended position, in which the distal end of the push rod is adjacent or slightly beyond the distal end of the shaft.

It is always desirable to simplify the insertion process for push-in, arrow-like implant devices. Accordingly, it is an object of this invention to develop a tissue repair system incorporating a cannulated push-in implant or tissue anchor device, preferably bioabsorbable, and a simplified insertion apparatus, preferably operable by one hand.

It is also generally an object of this invention to provide a tissue anchor inserting device and method for guiding and inserting a cannulated tissue anchor into position at a surgical site.

It is another object of this invention to provide an elongated inserting device for receiving therein a cannulated tissue anchor, preferably at its distal end.

It is still another object of this invention to provide an elongated inserting device suitable for endoscopic procedures and capable of being operated from its proximal end.

It is also an object of this invention to provide a tissue anchor inserting system which facilitates the assembly of an inserting device with a cannulated tissue anchor.

It is yet another object of this invention to provide a system incorporating a single use subassembly for retaining a tissue anchor and associated insertion components and a reusable activating instrument for receiving the subassembly and inserting the tissue anchor into place at a site of implantation.

It is an additional object of this invention to provide a reusable activating instrument having selectively interchangeable cartridges design to adapt the instrument for use with different size tissue anchors.

SUMMARY OF THE INVENTION

These and other objects are accomplished by the preferred embodiment of the system disclosed herein which comprises a surgical instrument for inserting a cannulated surgical implant into a surgical site. The instrument comprises a surgical implant assembly comprising an elongated needle for slidably receiving the implant thereon, an elongated pusher for pushing the implant distally from the needle and an elongated tube for slidably retaining the implant, the needle and the pusher. A sequential mechanism is used for first moving the needle distally a first predetermined distance, and then moving the pusher to thereby slide the implant along the needle and distally from the tube. In one preferred embodiment, the sequential mechanism comprises a trigger attached to a pawl means and a slide member associated with the needle and another pawl means on slide member associated with the pusher. Each slide member has one or more ratchet edges for being sequentially engaged by its associated pawl means to move the slide distally a predetermined distance. The slide members are connected respectively to the proximal ends of the needle and pusher so movement of a slide causes movement of the needle and pusher.

In another preferred embodiment, the sequencing mechanism comprises an activating cartridge having one cam track for engaging a cam roller on the slide member associated with the needle and another cam track for engaging the slide member associated with the pusher. The cartridge is received in a vertical sliding channel and is incrementally moved in this channel by a trigger mechanism which sequentially engages teeth on a vertical surface of the cartridge to move the cartridge in discrete steps. This cartridge motion causes the cam rollers to follow in their respective tracks, thereby moving the needle and pusher distally in the desired sequence.

The invention also resides in the method of using the aforementioned instrument to place a cannulated surgical implant at a surgical site with an instrument suitable for single-handed use.

BRIEF DESCRIPTION OF THE DRAWINGS

FIG. 19 is a side elevation view of one side of a representative activating cartridge for use with the instrument of FIG. 14.

FIG. 20 is a side elevation view of the other side of the cartridge of FIG. 19.

FIG. 21 is a rear elevation view of the cartridge of FIGS. 19 and 20.

DESCRIPTION OF THE PREFERRED EMBODIMENT

Figure 1:
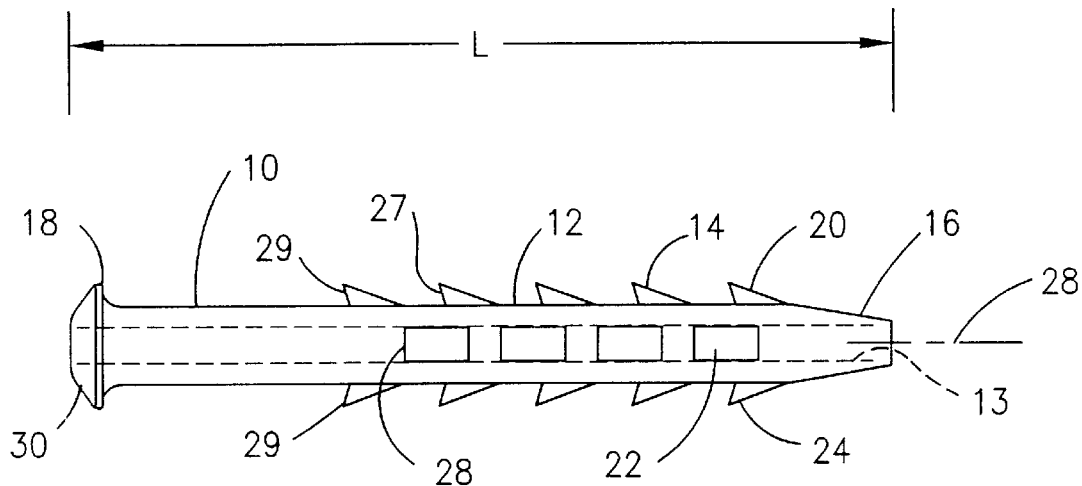
FIG. 1 is a side elevational view of a prior art cannulated surgical implant suitable for use with an insertion system constructed in accordance with the principles of this invention.
Figure 2:
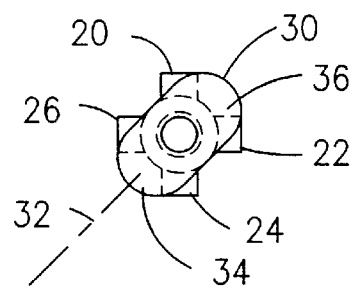
FIG. 2 is a left end view of FIG. 1.

Referring now to FIGS. 1 and 2 there is shown a cannulated tissue anchor 10 described in the aforementioned co-pending patent application Ser. No. 09/141,175. This anchor is intended to be used with the insertion systems shown in FIGS. 3 through 16, constructed in accordance with the principles of this invention.

Anchor 10 comprises an elongated shaft 12 having an axial bore 13 and a plurality of barbs 14 situated on its external surface and extending between a distal end 16 and a proximal end 18. The barbs are arranged in four linear rows 20, 22, 24 and 26 with rows 20 and 24 having an equal number of barbs in each row and rows 22 and 26 having a lesser number of barbs in each row. The barbs in adjacent rows are longitudinally staggered to enable the tissue anchor to resist rotation about its axis 28. The anchor may be made in various lengths and diameters with various numbers of barbs and with various lengths of smooth, barb-free shafts between the proximal most barbs 29 and proximal end 18. In the preferred embodiment, all rows have three barbs each if the anchor length L is 10 mm. If the anchor length L is 13 mm or 16 mm, rows 20 and 24 each have five barbs and rows 22 and 26 each have four barbs (as shown in FIG. 1). The distal-most barbs in all cases are situated at the same distance from distal end 16.

Anchor 10 further comprises a head 30 at its proximal end 18. In the preferred embodiment, head 30 is a generally flat, oval structure having a major axis 32 which is angled relative to the plane of rows 20 and 24 as best seen in FIG. 2. This intentional misalignment of the axis of head 32 enables it to abut tissue in the areas adjacent to the distally facing sides of portions 34 and 36 of the head. It will be understood that as the barb rows 20, 22, 24 and 26 are pushed into tissue to be treated at the surgical site, the tissue is necessarily pushed aside or slightly deformed in the areas adjacent the barbs and along the lines of the barbs. If the head axis 32 were to be aligned in the plane of two diametrically opposed rows of barbs, for example, the head may have a tendency to migrate distally along the tissue defects created by the barb rows. The intentional misalignment of the axis of the head prevents the distal advancement of the barb because the head lies adjacent "virgin" tissue which is not subject to deformation by the barb rows. Thus, it will be understood that the particular shape and orientation of head 30 enables the profile of the head to be minimized while also minimizing the possible migration of the tissue anchor at or from the surgical site. This beneficial orientation of the major axis of the head would also apply to tissue anchors in which the barbs might be arranged in helical rows.

Referring now to FIGS. 3 through 12, there is described a preferred tissue anchor inserter system for inserting a cannulated tissue anchor (such as anchor 10) and the method for using same. The system comprises an inserting instrument 100, shown in FIG. 3 and preferably intended to be reused, and a surgical implant assembly 200, best seen in FIG. 5 and preferably intended for single use. Assembly 200 is shown with a straight distal end 206, (described below), although it will be understood that various simple or compound curves could be formed in the distal end to enable the implant to be endoscopically or otherwise delivered to a variety of surgical sites. An example of possible curves is shown in the aforementioned co-pending patent application.

Figure 5:
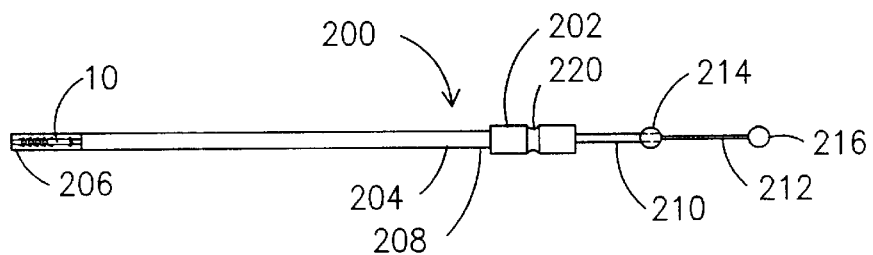
FIG. 5 is a side elevation view of an implant subassembly used in the instrument of FIG. 3, partially in cross-section.

As shown in FIG. 5, surgical implant (tissue anchor) assembly 200 comprises a tubular body 202, an elongated tubular shaft 204 extending from one end of the body and having a distal end 206. End 206 may be provided with a window (not shown) in the cylindrical wall to enable a user to see the position of the anchor. The proximal end 208 of shaft 204 is secured to the distal end of mounting body 202. An elongated tubular pusher 210 is slidably received within the lumen of tube 204 and an elongated needle 212 is slidably received within the lumen of pusher 210. In the preferred embodiment, needle 130 may be made of a stainless steel or a memory alloy such as nitinol and has a diameter of 0.025 inches (0.635 mm) to fit in anchor bore 13 which has a diameter of 0.026 inches (0.660 mm). Pusher 210 has a body 214 formed at its proximal end, body 214 having an axial bore to receive needle 212 therethrough. Needle 212 has a body 216 formed at its proximal end. Body 214 is used to move pusher 210 within tube 204 and body 216 is used to move needle 212 within pusher 210 and relative to tube 204.

Assembly 200 may be produced pre-loaded with one of a variety of tissue anchor sizes and, as mentioned above, with a variety of curves. A selected assembly may easily be installed in instrument 100 by engaging tubular mounting body 202 in a complementarily shaped portion of the instrument and by engaging body members 214 and 216 with their respective receptacles, as will be understood below. Body 202 has along its length a non-circular profile in a plane perpendicular to the axis of shaft 204, and has an annular groove 220. In the preferred embodiment, the non-circular profile is a rectilinear profile which enables the assembly 200 to be inserted in any of a plurality of discrete positions. In the preferred embodiment body 202 has four longitudinally extending sides enabling it to be positioned in four positions, 90° apart. Groove 220 assists in longitudinally aligning and retaining the assembly within the instrument.

Figure 3:
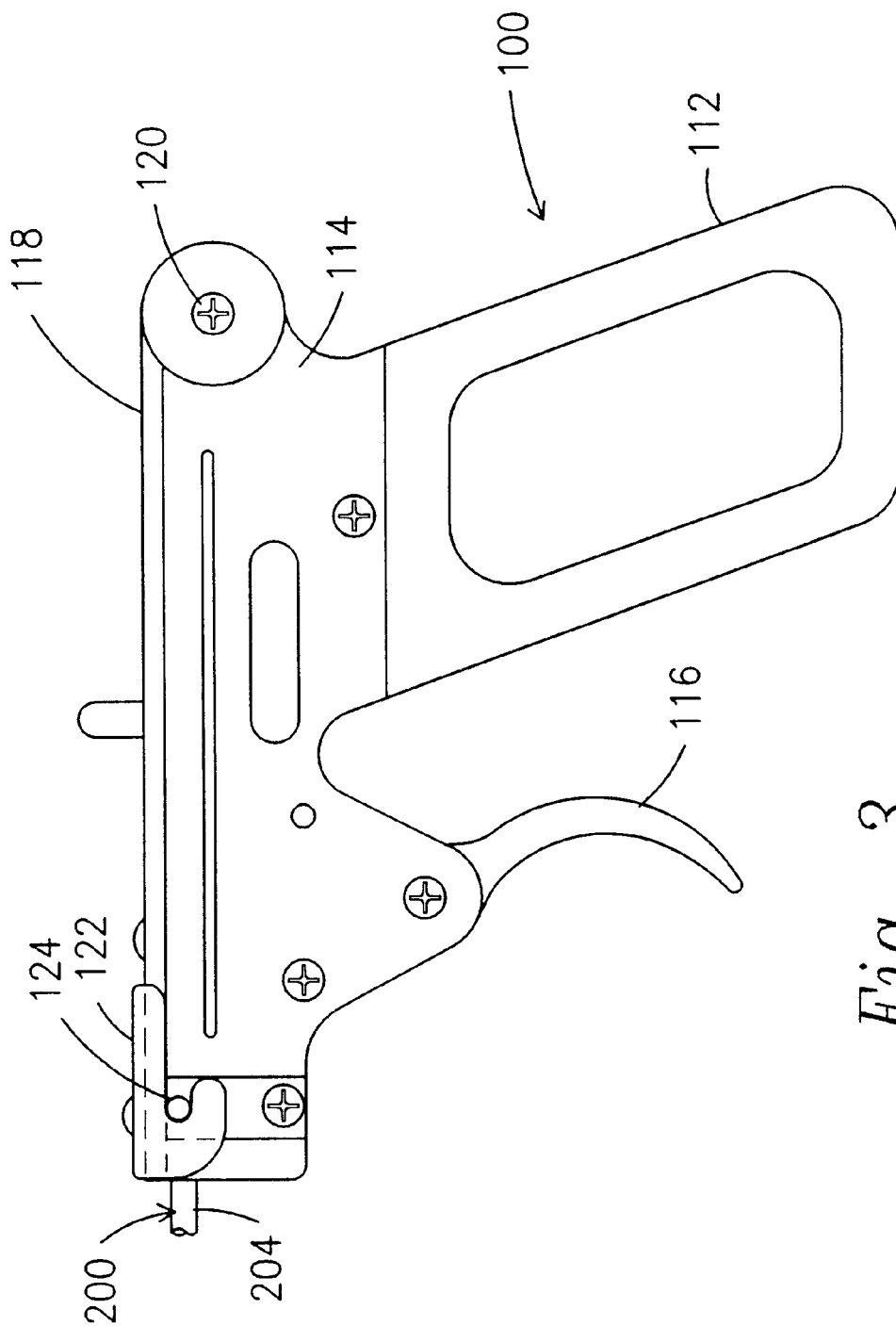
FIG. 3 is a side elevational view of a cannulated implant insertion device constructed in accordance with the principles of this invention.
Figure 4:
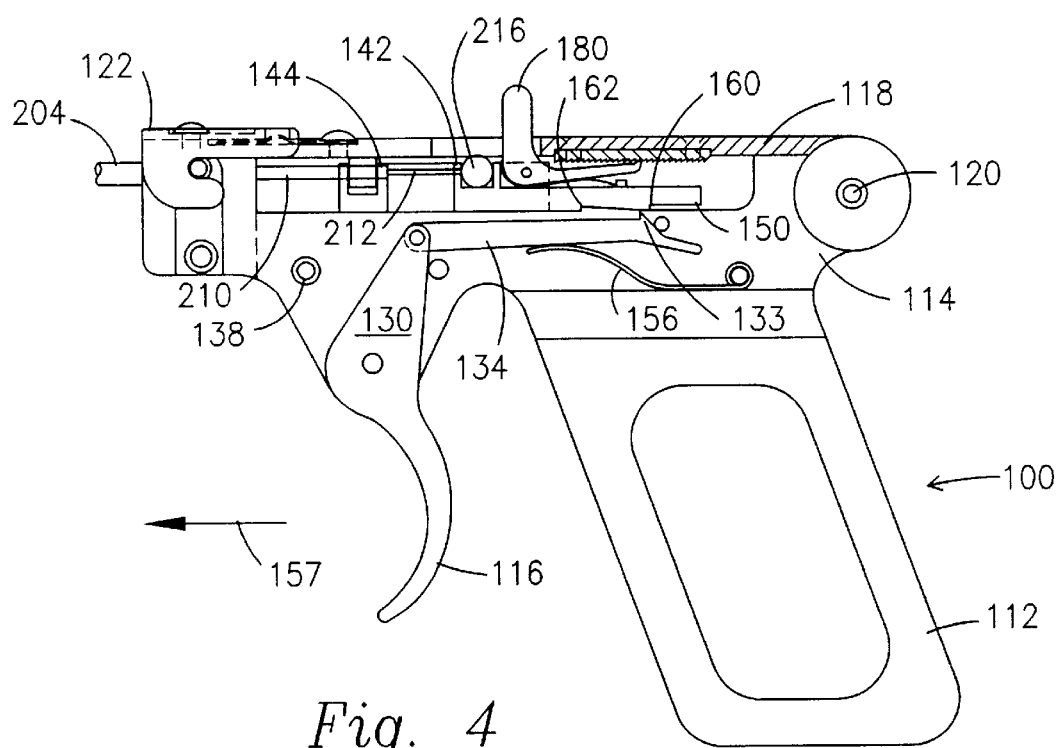
FIG. 4 is a diagrammatic view of the instrument of FIG. 3 showing the internal components.

Referring to FIGS. 3 and 4 there is shown a side elevational view of a pistol-grip inserter instrument 100 used for inserting a surgical implant 10 situated at the distal end of surgical implant assembly 200. Inserter 100 comprises a handle portion 112, a body portion 114 and a trigger 116. Body portion 114 has a top cover 118 which is pivotable about a transverse pivot pin 120 and which may be locked in place by a spring-loaded, longitudinally slidable locking plate 122 which selectively engages a pair of locking pins 124, only one of which is shown in FIG. 3. Cover 118 may be opened to provide access to the interior of the instrument to load a surgical implant assembly 200 into position. When properly loaded, assembly 200 is received within a sequential activating mechanism 140 (best seen in FIG. 6) situated in the body 114 of instrument 100. Activating mechanism 140 comprises a receiving member 142 for receiving the proximal end 216 of needle 212 and also includes a receiving member 144 for receiving the proximal end 214 of pusher 210. Receiving members 142 and 144 are situated at the proximal ends of longitudinally slidable members 150 and 152, respectively, and serve to engage the needle and pusher, respectively, so that motion of the slidable members effects motion of the needle and pusher. Each of the slide members 150 and 152 is provided with a ratchet mechanism in the form of transverse edges on its bottom surface in order to engage pawl members 134 and 132, respectively, as will be understood below. Pawl members 132 and 134 have surfaces 133 and 135, respectively, to engage edges on the sides. Trigger 116 is attached to a lever 130 which is in turn attached to the pair of pawl members 132 and 134.

Assembly 200 is intended to be received within instrument 100 in a manner which will be understood below. The instrument is designed to insert the implant according to the method described in the aforementioned co-pending patent application Ser. No. 09/141,175. Basically, as will be better understood below, once the loaded assembly is in position in the instrument and situated at the surgical site, the method steps are as follows: the needle 212 is first moved distally relative to the tube 204 in order to locate the position at the surgical site where the implant 10 will be inserted. Pusher 214 is then moved distally along the needle 212 in order to push implant 10 from the needle into the surgical site. The method steps are achieved by the instrument by simply moving its trigger cyclically through a number of trigger pulls.

Figure 6:
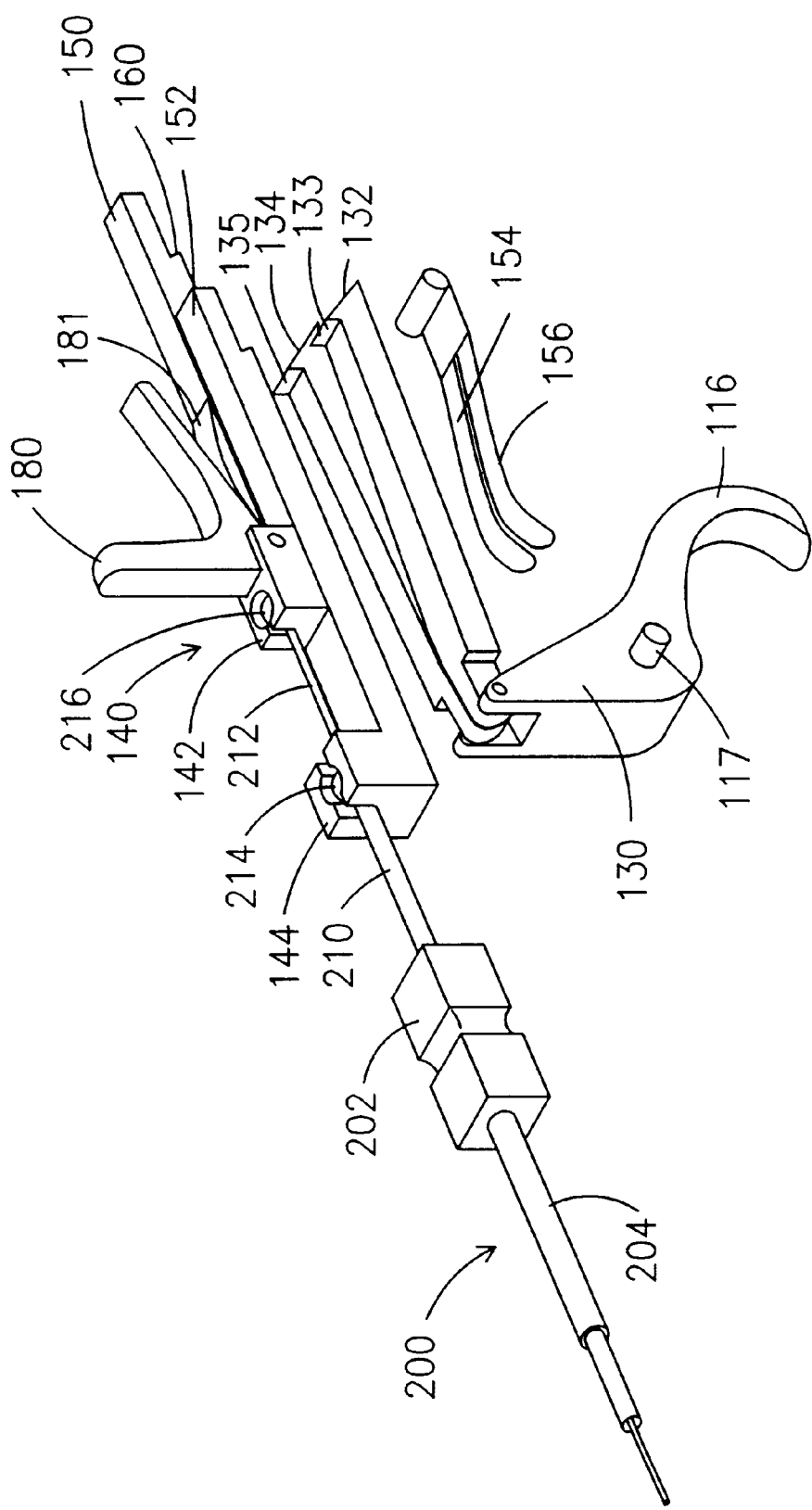
FIG. 6 is a diagrammatic front perspective view of the operating mechanism within the instrument shown in FIG. 4 which sequentially moves the various elements of the implant subassembly shown in FIG. 5.

The explanation of the operation of the inserter 100 will be best understood by reference to FIG. 6 showing a diagrammatic representation of the instrument's internal components. The pivoting motion of trigger 116 about pivot pin 117 effects a reciprocating longitudinal motion of both pawl members 132 and 134. Spring members 154 and 156 assure that pawl members 132 and 134 engage and stay in engagement with the ratchet edges on the bottom surfaces of slide members 150 and 152, and a spring (not shown) is used to bias trigger 116 in the direction of arrow 157. As the trigger is cyclically squeezed by a user the pawl members will sequentially engage the ratchet edges of the slide members. For example, instrument 100 is designed so that the first pull of trigger 116 will cause needle pawl member 134 to engage a ratchet edge of needle slide member 150 in order to move member 216 a predetermined distance distally, thus advancing the distal end of the needle from the distal end of tube 204. Subsequent release of trigger 116 will move both pawl members 132 and 134 proximally in order to position pusher pawl member 132 for engagement with a ratchet edge on pusher slide member 152 to move member 214 distally a predetermined amount in order to urge pusher 210 distally along needle 212.

Figure 7:
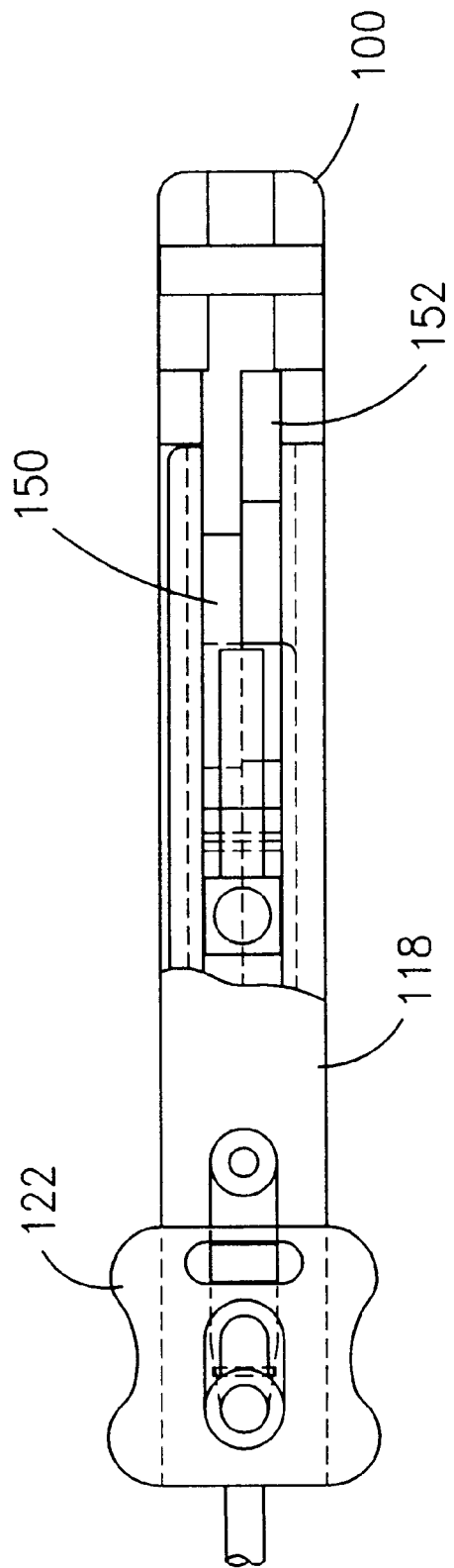
FIG. 7 is a top plan view of the instrument of FIG. 4, partially in cross-section.
Figure 8:
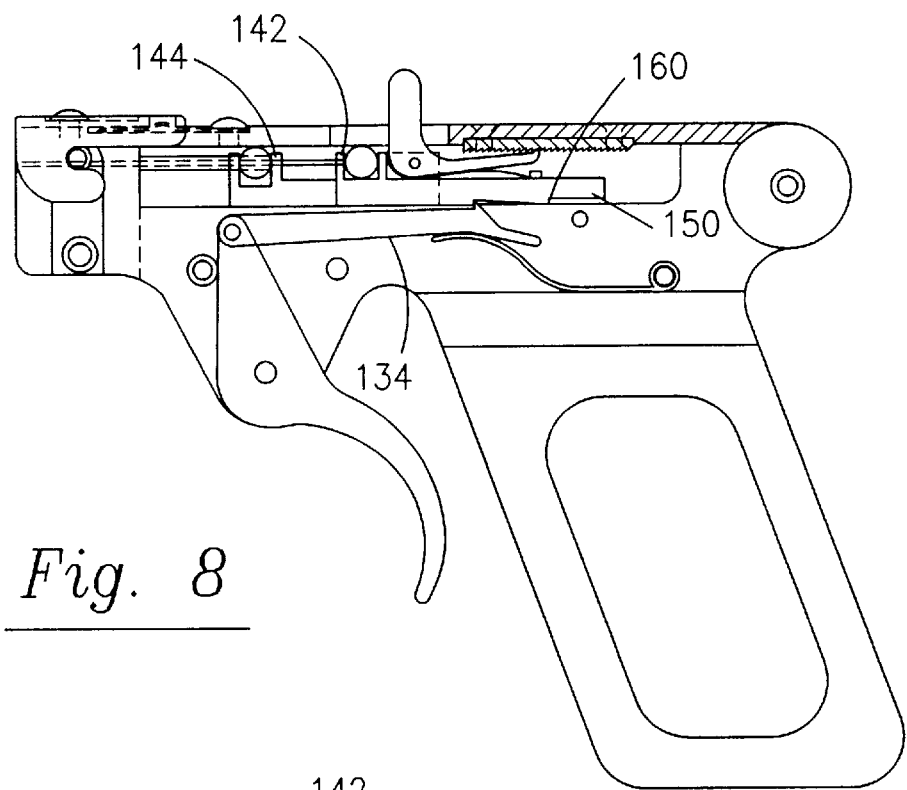
FIGS. 8–13 are side elevation views of the inserting instrument in various stages of use.
Figure 9:
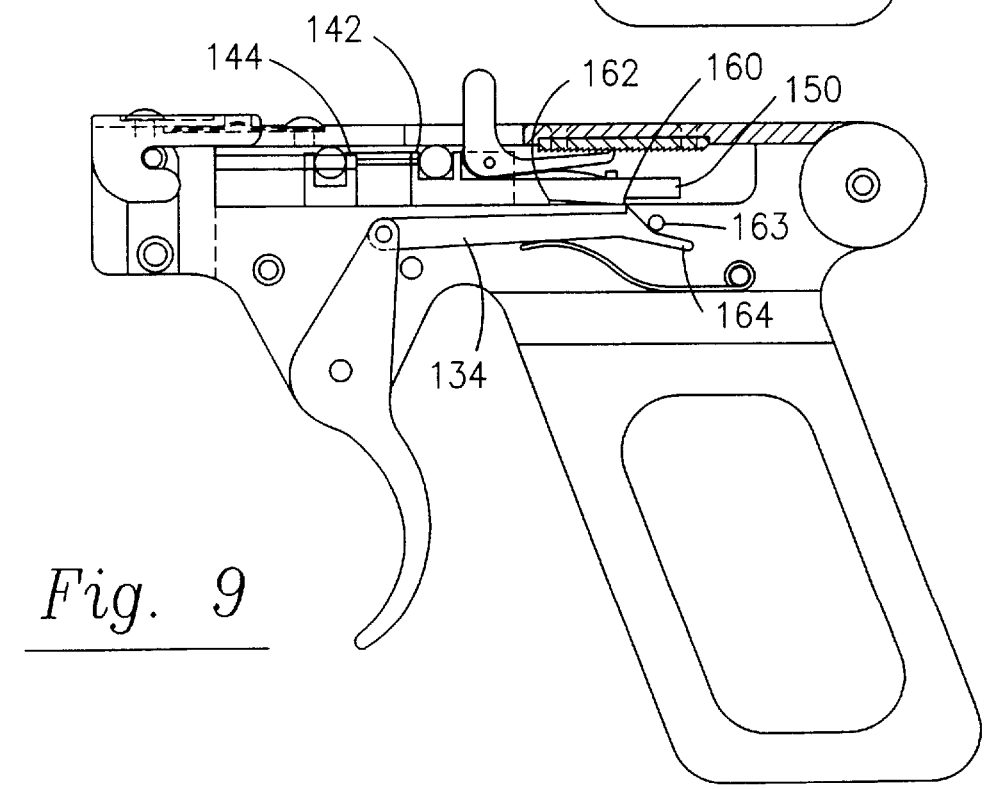
Figure 10:
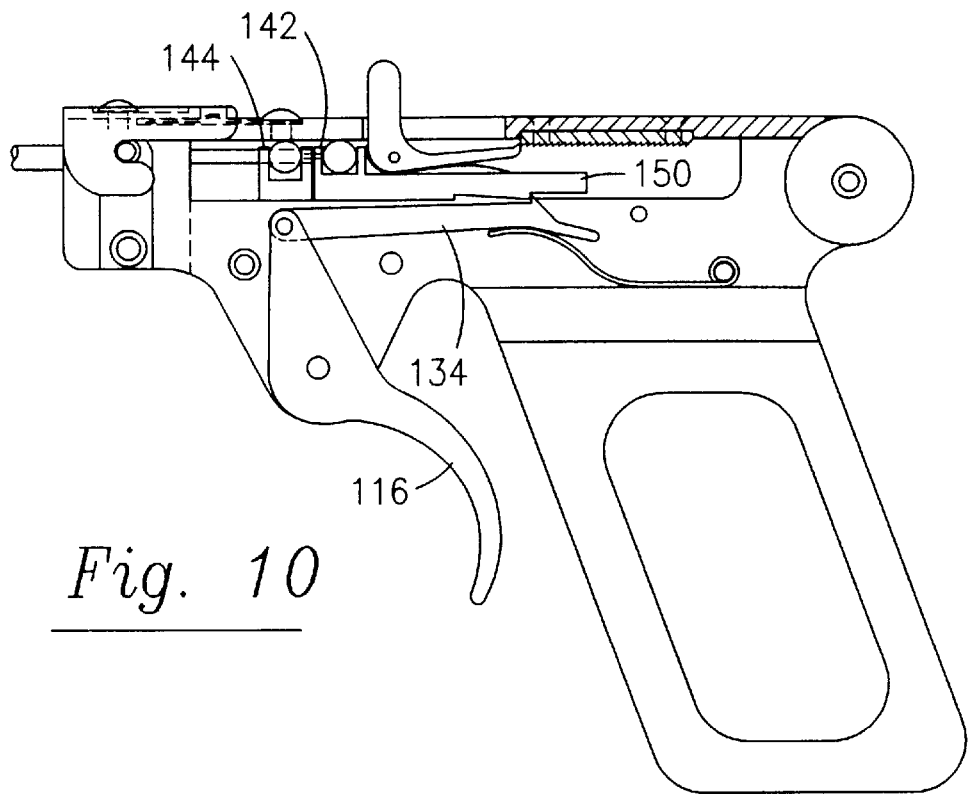
Figure 11:
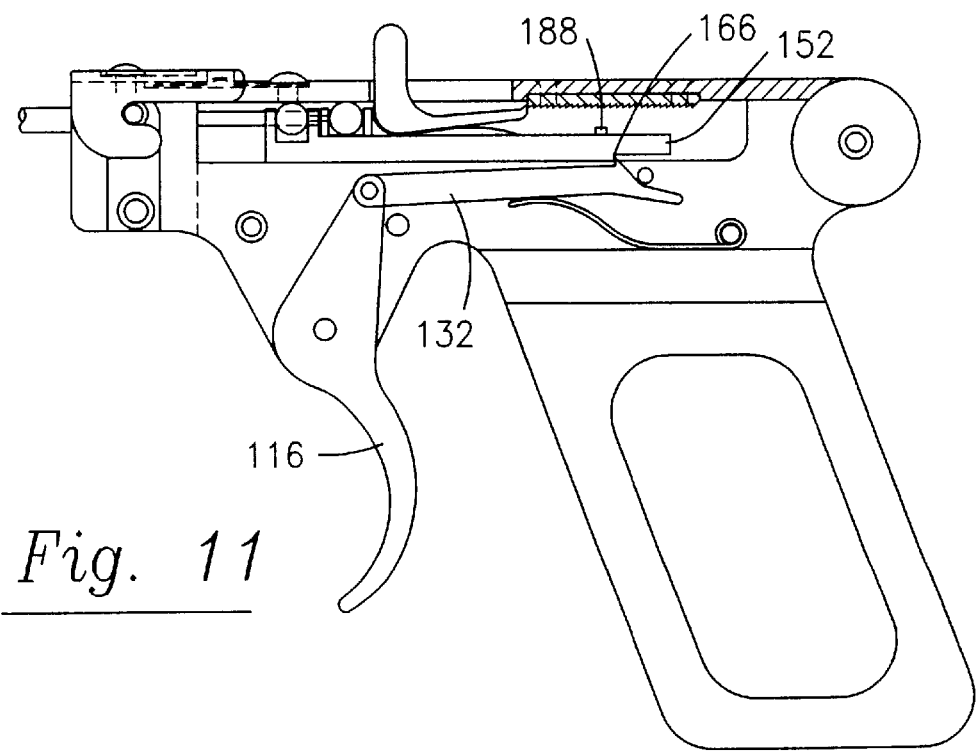
Figure 12:
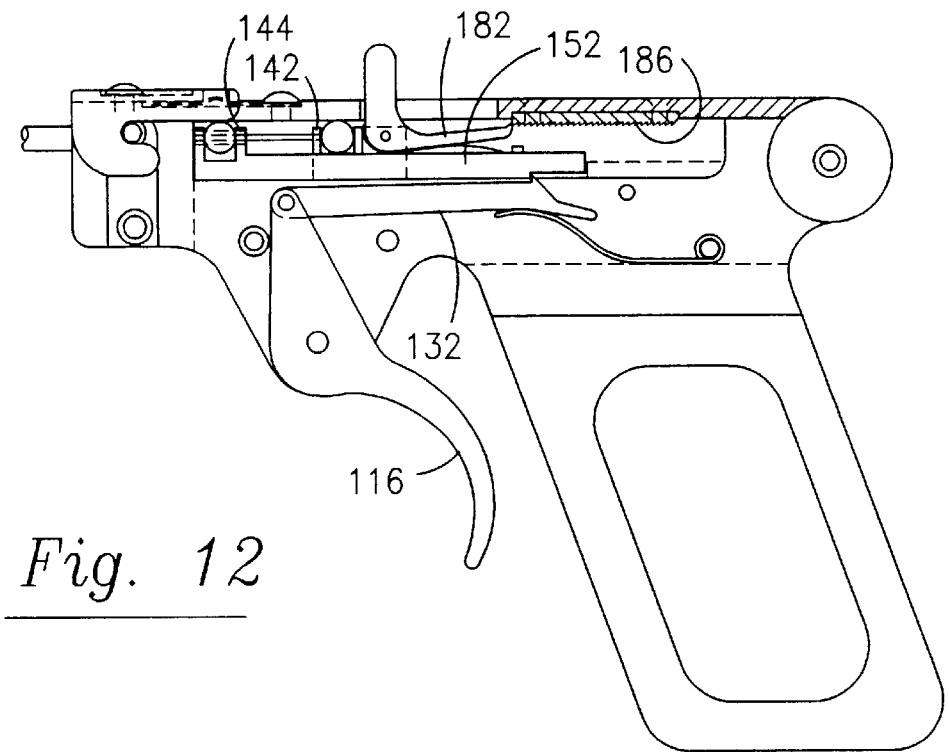
Figure 13:
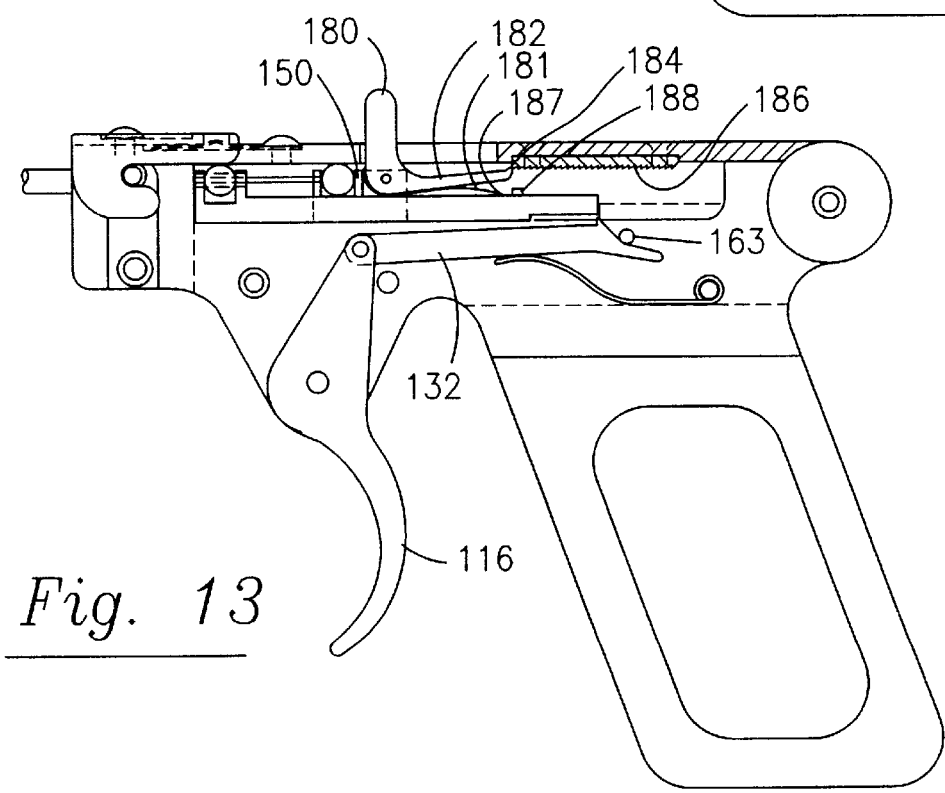
Figure 14:
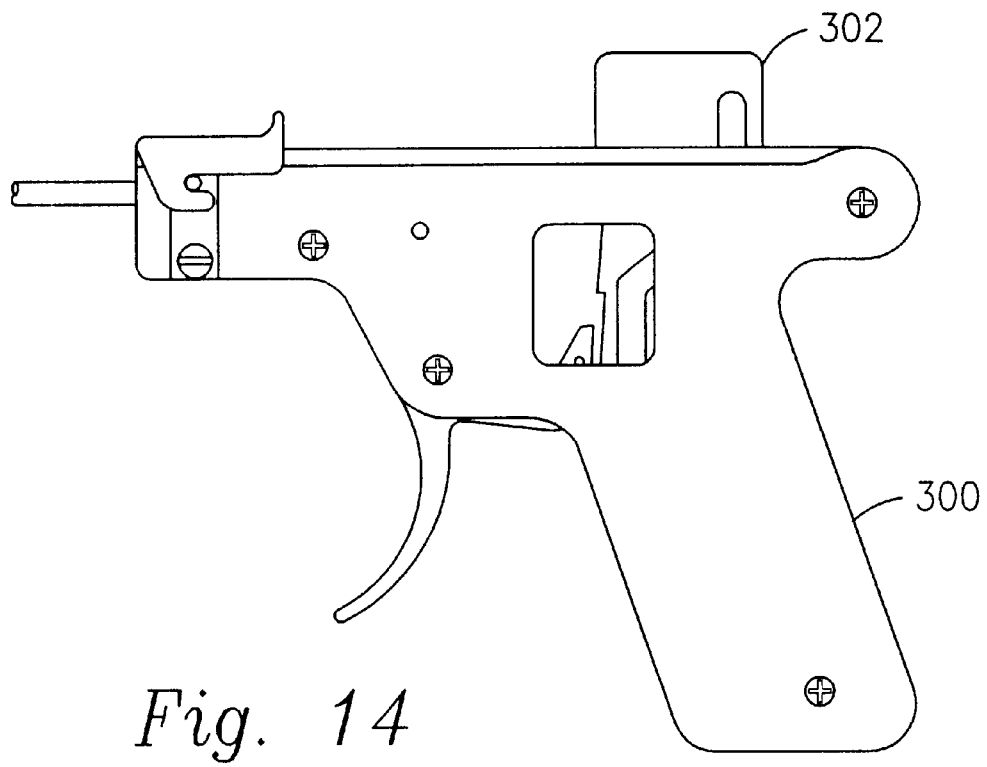
FIG. 14 is a side elevation view of an alternate embodiment of an implant inserting instrument for use with the implant subassembly of FIG. 5.
Figure 15:
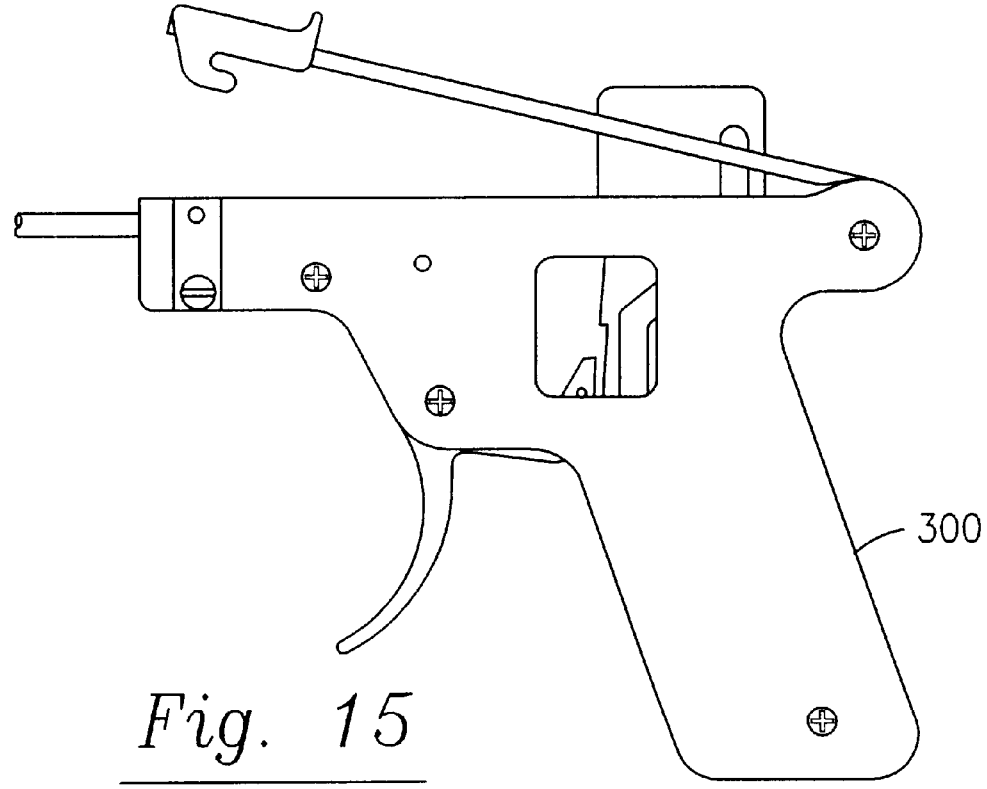
FIG. 15 is a view of the instrument of FIG. 13 with its top open.

In the preferred embodiment the trigger is pulled several times in order to effectuate the sequential motion of the various components of implant assembly 200. The sequence of operations is best seen by reference to FIG. 4 and FIGS. 8 through 13. These drawings are views taken through sections of FIG. 7 showing a partially cross-sectional top plan view of instrument 100. Section D—D is through the instrument along needle slide 150 and section E—E is through pusher slide 152. While FIG. 7 shows the slides in representative positions, FIGS. 4 and 8–13 show the slides in positions associated with the sequential trigger pulls used to insert the implant. For clarity, some elements are omitted in some drawings. All these drawings show the instrument loaded with a pre-loaded surgical implant assembly 200. The latter is loaded with an implant and is placed into instrument 100 by moving latch 122 distally to disengage it from pins 124, opening cover 118 by pivoting it around pin 120, engaging body 202 with a corresponding channel (not shown) in the top of the instrument, engaging members 214 and 216 with receptacles 144 and 140, respectively, and closing cover 118. As best shown in FIG. 4 through section D—D, the beginning position of the instrument and one of the first steps of its method of use is shown wherein needle pawl member 134 is situated just distally of a ratchet edge 160 on needle slide member 150. Simultaneously, pusher pawl member 132 is situated against a flat surface on slide 152, proximal to any ratchet edge so that proximal motion of member 132 will not move the pusher. Thus, the first pull of trigger 116 will cause needle pawl member 134 to engage ratchet edge 162 in order to move needle 212 distally a predetermined amount while the pusher pawl will not move the pusher. The relationship between the allowable range of travel of needle pawl member 134 and the starting position of edge 162 is such that after the first trigger pull the needle is moved distally a distance of approximately 2 mm before the distal motion of pawl 134 is stopped by the contact of lever 30 with stop pin 138. This motion is shown in FIG. 8 as position 2. As shown in FIG. 9, position 3, the trigger is then released in order to retract needle pawl member 134 to its proximal-most position (and pusher pawl 132) to enable it to now engage ratchet shoulder 160. Transverse pin 163 is situated in the rearward path of both pawl members to engage the ends 164 to move the proximal ends of the pawls down to enable them to engage the appropriate ratchet edge. As shown in FIG. 10, position 4, as the trigger 116 is squeezed the needle slide member 150 is moved distally until its needle receiving member 142 contacts pusher receiving member 144 and pushes it distally approximately 1 to 1.5 mm to move the ratchet edge of the pusher slide 152 so it can be engaged by the pusher pawl 132 on the next trigger pull. At this point, the needle 212 will be extended from the distal tip of the tube 204 by a predetermined distance, this distance being that which is required to insert the particular size implant in assembly 200. As shown in FIG. 11, position 5, now through section E—E, the release of trigger 116 will enable pusher pawl member 132 to retract sufficiently to engage ratchet edge 166 on pusher slide 152. As shown in FIG. 12, position 6, squeezing the trigger once again causes the pusher slide 152 to urge the pusher receiving member 144 a predetermined distance distally in order to push the implant into the site of implantation. During this motion the needle receiving member 142 and the needle slide 150 are prevented from moving distally by the engagement of ratchet lever 182 with one way rack 186, further explained below. As shown in FIG. 13, position 7, release of trigger 116 repositions the trigger and the pawl members 132 and 134 into their starting positions with the latter moved downwardly by pin 163. After the instrument is removed from the surgical site, the now-depleted assembly 200 may be removed and discarded (or re-loaded if it is made reusable). Pulling reset/friction lever 180 proximally (either prior to removing the instrument from the body or after) will reset the needle and pusher slide members (to the start positions shown in FIG. 4) to enable the instrument to be loaded with a new implant assembly in order to begin the process again. Lever 180 is pivotably attached to needle sliding member 150 and is biased upwardly by spring 181 so its integral ratchet lever arm 182, having a pawl tip 184, is urged into engagement with one-way rack 186. Lever 180 serves a two-fold purpose. Not only does it enable grasping the sliding member 150 to pull it back, but with lever arm 182 provides a frictional drag to keep the needle sliding member from being inadvertently moved distally, especially during distal motion of the pusher slide. Spring 181 has a free end 187 which extends laterally over slide 152 to engage pin 188 when lever 180 is pulled proximally, thus pulling slide 152 as well.

While the method described above can be initiated by the manual loading of a single cannulated tissue anchor assembly onto the insertion device, a plurality of tissue anchors may alternatively be held in a modified device (not shown) which would sequentially load an anchor into position at the distal end of the anchor assembly tube so that a plurality of anchors could be applied without having to remove the instrument to reload another single tissue anchor assembly.

An alternate embodiment of the tissue anchor inserter system is shown in FIGS. 14–22 depicting inserting instrument 300 which is designed to operate with surgical implant assembly 200. The main sequence of operations of instrument 300 is the same as that of instrument 100, however, instrument 300 utilizes a cam driven means to effect motion of the components. While individual cams and cam followers could be used, in the preferred embodiment an interchangeable activating cartridge 302, best seen in FIGS. 19–22, is used as a selectable, interchangeable cam track interface between the instrument's trigger and the implant assembly. As will be understood below, a plurality of activating cartridges 302 may be produced, each with different cam track profiles to make each individual cartridge suitable for inserting a tissue anchor of a given length. For example, while FIGS. 19 and 21 show both sides of a cartridge suitable for use with 16 mm implants, 10 mm and 13 mm cartridges could be produced with cam tracks of similar but different profiles.

Referring to FIGS. 14–18, instrument 300 comprises a trigger assembly 316 which is adapted to incrementally move cartridge 302 upwardly in channel 320 extending vertically through the instrument handle 312. An opening 321 through the instrument facilitates cleaning and enables visualization of some internal components. Trigger assembly 316 comprises trigger 322 which is pivotably secured to the body of the instrument by pivot pin 324 and has a lever arm 326 extending from it at approximately 90°. A pawl lever 328 is pivotably secured by pin 336 to the end of lever arm 326. A spring (not shown) is used to bias trigger 322 in the distal direction shown by arrow 332, thus urging lever arm 326 and pawl lever 328 down against fixed transverse stop pin 338 which also limits the proximal motion of the pawl lever. Another transverse pin 339 extends through the end of pawl lever 328 to rest against the bottom edge of opening 321. Spring 334 (seen only in FIG. 17) is used to bias pawl lever 328 clockwise about pin 336. It will be understood that as trigger 322 is pulled proximally, pawl lever 328 will be urged upwardly, maintaining contact with the distally facing surface of cartridge 302, until the trigger assembly ultimately reaches its proximal most and upward most position shown in FIG. 17.

Figure 16:
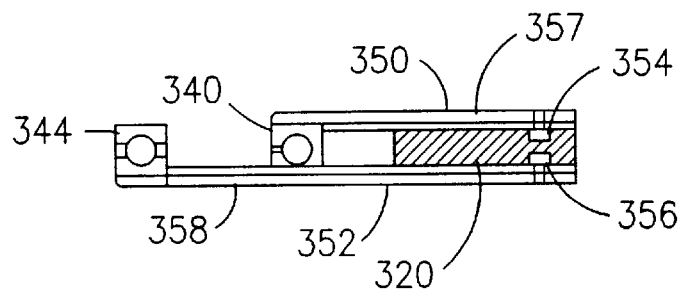
FIG. 16 is a diagrammatic top plan view of a portion of the instrument of FIG. 14 showing some of its internal components; namely, the needle and pusher slides, with the top cover removed.
Figure 17:
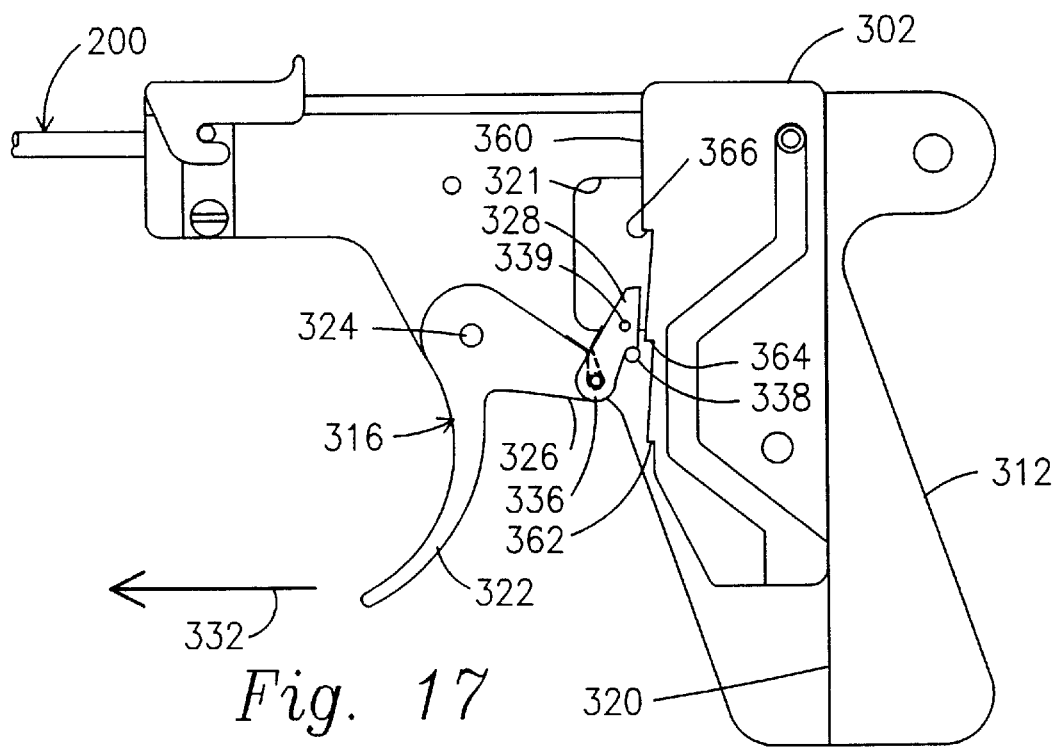
FIG. 17 is a side elevation view of the instrument of FIG. 14 partially in cross-section to show the positions of the trigger and cartridge during one stage of operation.
Figure 18:
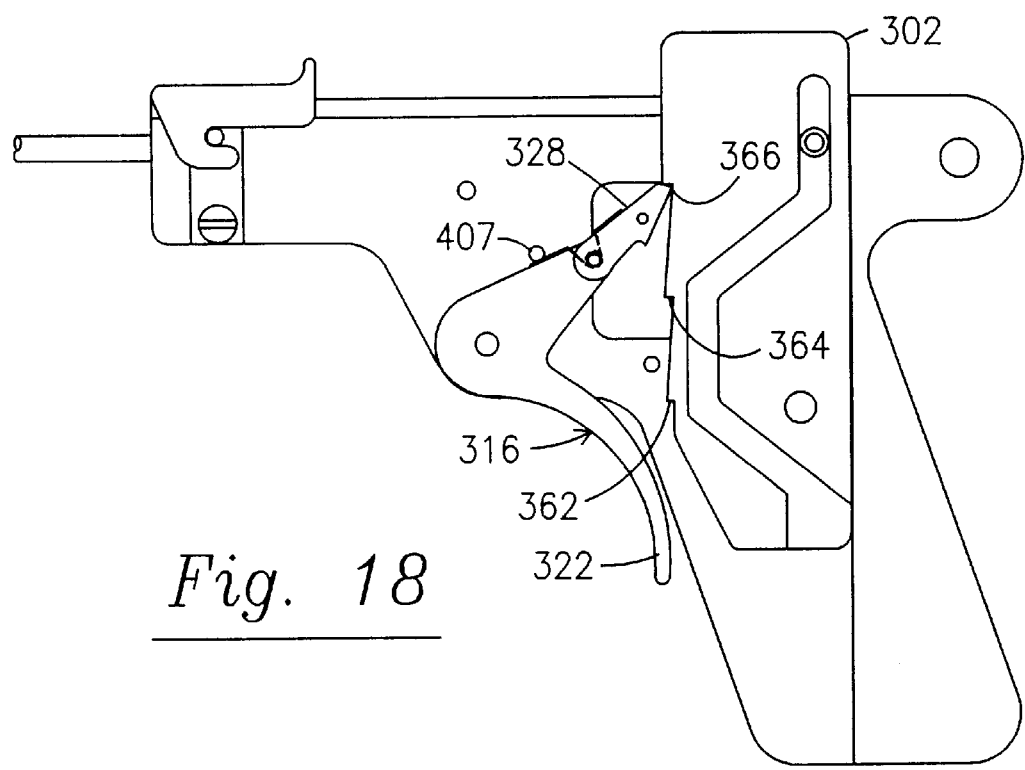
FIG. 18 is similar to FIG. 17 but shows another stage of operation.

Instrument 300 also comprises needle sliding member 350 and pusher sliding member 352 similar in function to their counterparts in instrument 100. Attached to the distal ends of slide members 350 and 352 are receiving members 340 and 344 (comparable to members 140 and 144, respectively). Attached to the proximal ends of slide members 350 and 352 are cam followers in the form of rollers 354 and 356, respectively, as best seen in FIG. 16.

Each cam roller is inwardly directed into channel 320 so that, when a cartridge 302 is inserted into the channel, each cam roller will be received in and follow a cam track on an associated side of the cartridge. Slide members 350 and 352 each have a longitudinally extending rib 357 and 358, respectively on their laterally outward sides, these ribs enabling the members to slide within longitudinal grooves (not shown) within the instrument. It will be understood that the channel 320 extends through the space between the distal sides of the slide members and the top cover of the instrument has an aperture in this area to permit cartridge movement.

All cartridges 302 operate similarly and, therefore, the principles of operation will be explained by reference to the 16 mm cartridge 302 shown in FIGS. 19–22. Cartridge 302 is a planar, rectangular solid member having a distally facing front side edge 360, provided with a plurality of spaced ratchet edges or teeth 362, 364 and 366, a flat top side edge 370, a proximally facing back side edge 372 and a bottom side edge 374. All sides 360, 370, 372 and 374 extend between left side surface 380 and right side surface 382. Cartridge 302 is intended to slide vertically within instrument 300 within channel 320 and is slidably maintained within this channel by a pin 384 received within a vertical groove (not shown) in the side wall of the channel. Bottom side 374 has a tapered front surface 388 which facilitates cartridge insertion and ultimate fit within handle 312. Sides 380 and 382 are provided with vertically extending cam tracks A and B, respectively, each track having a predetermined profile designed to control its associated cam rollers in a prescribed manner. Tracks A and B have cam track openings 390 and 392, respectively, to facilitate insertion of the cartridge into the instrument and insertion of the rollers into their respective tracks. To prepare instrument 300 for use with an implant subassembly loaded into place, cartridge 302 is pushed downwardly into channel 320 until the cam rollers 354 and 356 are each received in the top ends 400 and 402, respectively, of the cam tracks. A transverse stop pin (not shown) may be situated at the bottom of channel 320 to stop cartridge motion at a selected point.

Figure 22:
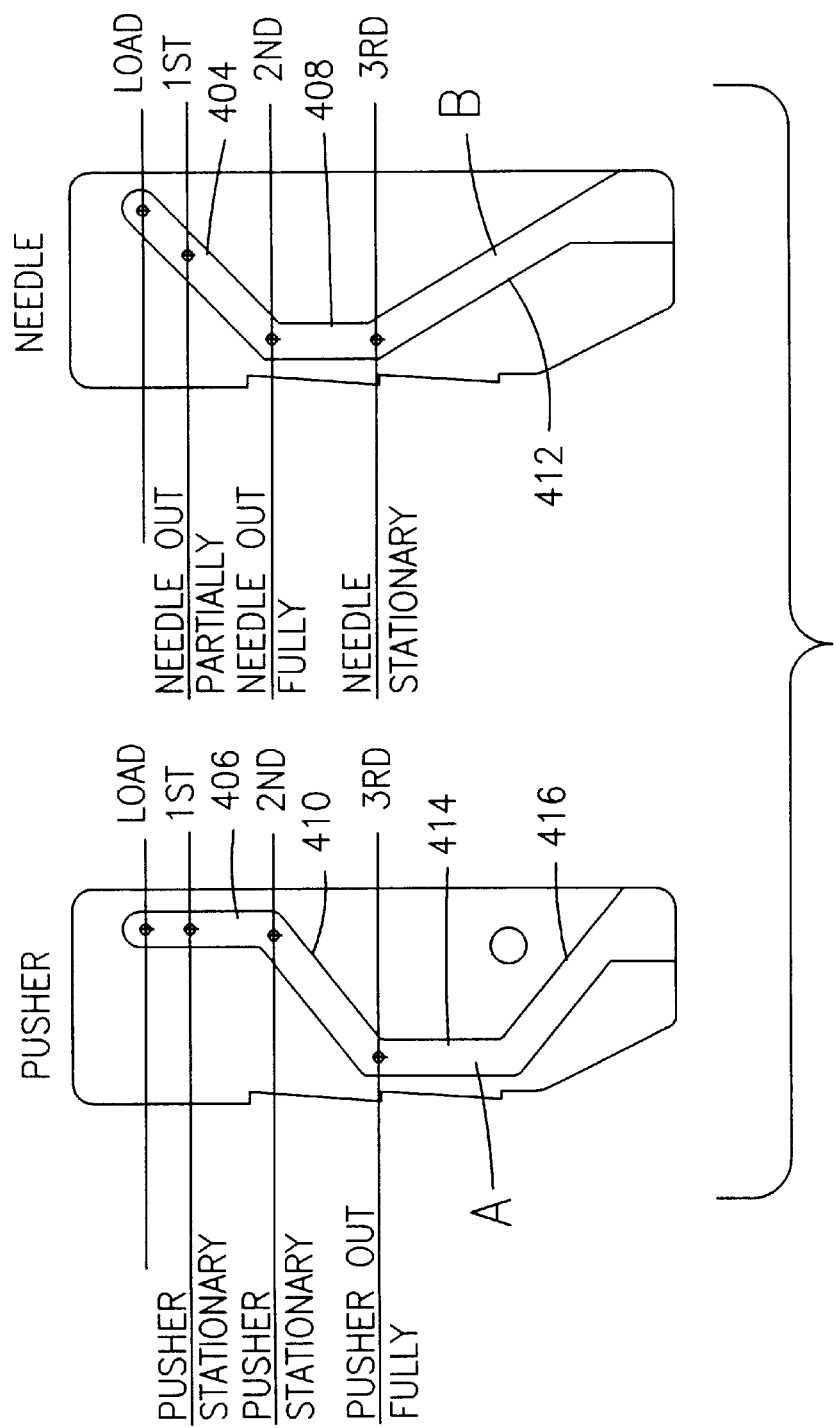
FIG. 22 is a composite view of the opposite sides of the cartridge of FIGS. 19 and 21 showing both cam tracks oriented in the same direction and showing the locations of the cam rollers correlated to successive trigger pulls.

Referring to FIGS. 17, 18, 19, 20 and 22, when cartridge 302 is at its bottom-most position (FIG. 17) pawl lever 328 rests adjacent distal side 360 at a point above tooth 364 and the cam rollers are at the "load" position in tracks A and B (FIG. 22). Consequently, the first trigger pull will move lever 328 upward into tooth 366 (FIG. 18) causing the cartridge to be pushed up, in turn causing needle cam roller 354 in track B to be pushed distally along track section 404 while pusher cam roller 356 remains stationary within vertical track section 406. The upward motion of the cartridge is stopped at the end of travel of pawl lever 328 (which is also limited by pin 407, FIG. 18). This motion corresponds to moving the needle distally a short distance (e.g. 2 mm) beyond the tip of implant assembly 200 in order to facilitate approximation of the tissue at the surgical site ($1^{st}$ position in FIG. 22). The trigger is then released to reset pawl lever 328 to the position shown in FIG. 17, but now below tooth 364 (not shown), and then pulled a second time to push the cartridge up a second time, in turn causing needle cam roller 354 in track B to be pushed further distally in track section 404 while pusher cam roller 356 still remains stationary in track section 406 ($2^{nd}$ position in FIG. 22). This motion, resulting in movement of the needle to the desired depth in the tissue, is stopped again by the end of the travel of pawl lever 328. (The ends of needle and pusher track sections 404 and 406 need not coincide exactly. For example, (by changing track dimensions), the needle cam roller could be placed partially into track section 408 while pusher cam roller is at the end of track section 406, thus providing an additional limitation to any needle movement back up track 404). The trigger is released again and pulled again to engage pawl lever 328 with tooth 362 to move the cartridge up a third time, in turn causing pusher cam roller 356 to be pushed distally by track section 410 while needle cam roller 354 remains stationary in vertical track section 408. This motion corresponds to pushing the implant distally from the needle ($3^{rd}$ position in FIG. 22). Track sections 412, 414 and 416 play no part in the delivery of the implant but aid in guiding the cam rollers to the upper portions of the tracks. It will be noted that tracks A and B may have curved track sections and may be arranged to accomplish a variety of sequential motions of two slidable members, horizontally or vertically. One may envision a plurality of cartridge sides of a polygonal cartridge, each having a cam track for controlling a like plurality of components.

While the preferred embodiment has been designed to produce a short extension of the needle tip from the delivery tube, this step is to facilitate approximation of the torn tissue to be repaired. This, in turn, requires three trigger pulls to accomplish the necessary sequential motions. It should be clear that if no short needle extension is needed or desired, an instrument could be designed to operate with just two trigger pulls: corresponding to the steps of needle penetration and pushing the implant. Conversely, if additional steps are desired, additional trigger pulls could be designed into the system.

It will be understood by those skilled in the art that numerous improvements and modifications may be made to the preferred embodiment of the invention disclosed herein without departing from the spirit and scope thereof.

What is claimed is:

1. A surgical instrument for inserting a cannulated surgical implant into a surgical site, the instrument comprising:

a surgical implant assembly comprising an elongated needle for slidably receiving said implant thereon, said needle having a proximal end and a distal end, an elongated pusher for pushing said implant distally from said needle, said pusher having a proximal end and a distal end, an elongated tube for slidably retaining said implant, said needle and said pusher, said tube having a proximal end and a distal end;

first moving means for moving said needle distally a first predetermined distance; and second moving means for moving said pusher distally a second predetermined distance to thereby slide said implant along said needle and distally from said tube.

2. A surgical instrument according to claim 1 wherein said elongated pusher comprises a cylindrical tube having an axially aligned bore for receiving said elongated needle therethrough.

3. A surgical instrument according to claim 1 further comprising a housing and wherein said first moving means comprises:

first activating means connected to said housing for selectively activating motion of said needle; and first slidable engagement means for connecting said needle to said first activating means;

and wherein said second moving means comprises:

second activating means connected to said housing for selectively activating motion of said pusher; and second slidable engagement means for connecting said pusher to said second activating means.

4. A surgical instrument according to claim 3 wherein said first activating means comprises:

a trigger movable between a first position and a second position; and a first pawl means for being moved by said trigger;

and wherein said first slidable engagement means comprises:

a first slidable member having a ratchet edge for being engaged by said first pawl means; and a first receiving member connected to said first slidable member for receiving said proximal end of said needle therein; and wherein said second activating means comprises:

a second pawl means for being moved by said trigger;

and wherein said second slidable engagement means comprises:
  a second slidable member having a ratchet edge for being engaged by said second pawl means; and
  a second receiving member connected to said second slidable member for receiving said proximal end of said pusher therein.

5. A surgical instrument according to claim 4 wherein said proximal end of said needle comprises a first mounting member and wherein said first receiving member is adapted to receive said first mounting member.

6. A surgical instrument according to claim 5 wherein said first mounting member is larger in size than the portion of said needle retained within said tube.

7. A surgical instrument according to claim 5 wherein said proximal end of said pusher comprises a second mounting member and wherein said second receiving member is adapted to receive said second mounting member.

8. A surgical instrument according to claim 7 wherein said second mounting member is larger in size than the portion of said pusher retained within said tube.

9. A surgical instrument according to claim 4 further comprising:
  sequencing means for enabling said trigger to be moved between said first and second positions a first time to move only said first slidable member and then moved a second time to move only said second slidable member.

10. A surgical instrument according to claim 3 further comprising:
  engagement means for connecting said proximal end of said elongated tube to said housing.

11. A surgical instrument according to claim 10 wherein said elongated tube has an axis and wherein said engagement means further comprises:
  selective orientation means for orienting said elongated tube in a selected one of a plurality of angular positions relative to its axis.

12. A surgical instrument according to claim 10 wherein said selective orientation means comprises a rectilinear member having a plurality of parallel longitudinally extending planar surfaces laterally spaced from each other on opposite sides of said tube; and
  rectilinear receiving means on said housing for receiving selected pairs of said planar surfaces to thereby hold said elongated tube in a selected orientation.

13. A surgical instrument according to claim 3 wherein said first and second activating means comprise a single trigger means movable sequentially between a first position and a second position to alternatingly activate said first and second activating means.

14. A surgical instrument for inserting a cannulated surgical implant into a surgical site, the instrument comprising:
  a surgical implant assembly comprising an elongated needle for slidably receiving said implant thereon, said needle having a proximal end and a distal end, an elongated pusher for pushing said implant distally from said needle, said pusher having a proximal end and a distal end, an elongated tube for slidably retaining said implant, said needle and said pusher, said tube having a proximal end and a distal end;
  first moving means for moving said needle distally a first predetermined distance, said first moving means comprising:
    a first cam means for producing a first predetermined motion of an element associated therewith;
    a first slide member comprising:
      means to engage said needle to enable motion of said first slide member to effect motion of said needle;
      first track means to enable said first slide member to move in a direction aligned with said distal end of said needle; and
      first cam follower means for following said first cam means;
  second moving means for moving said pusher distally a second predetermined distance to thereby slide said implant along said needle and distally from said tube, said second moving means comprising:
    a second cam means for producing a second predetermined motion of an element associated therewith;
    a second slide member comprising:
      means to engage said pusher to enable motion of said second slide member to effect motion of said pusher;
      second track means to enable said second slide member to move in a direction aligned with said distal end of said pusher; and
      second cam follower means for following said second cam means; and a housing for retaining said surgical implant assembly adjacent said first and second moving means.

15. A surgical instrument according to claim 14 wherein said first cam means comprises a first cam track having a first predetermined shape, wherein said first cam follower is movable along said first cam track, and wherein said second cam means comprises a second cam track having a second predetermined shape, wherein said second cam follower is movable along said second cam track.

16. A surgical instrument according to claim 14 wherein said first cam means and said second cam means comprise first and second cam tracks on opposing sides of a single cartridge member.

17. A surgical instrument according to claim 16 wherein said cartridge member is removable from said instrument.

18. A surgical instrument according to claim 16 further comprising a vertical channel for slidably receiving said cartridge member wherein said first and second cam follower means comprise first and second cam rollers, respectively, each roller facing the other and extending into said vertical channel in order to slidingly engage said first and second cam tracks, respectively.

19. A surgical instrument according to claim 16 further comprising:
  trigger means for incrementally moving said first cam means relative to said first cam follower means and said second cam means relative to said second cam follower means.

20. A surgical instrument according to claim 19 further comprising a trigger and cyclical sequencing means associated with said trigger for enabling repetitive motion of said trigger to effect said incremental motion.

21. A surgical instrument according to claim 20 further comprising:
  a plurality of spaced edges on said cartridge member;
  trigger means for incrementally moving said first cam means relative to said first cam follower means and said second cam means relative to said second cam follower means; and
  pawl means responsive to said trigger means for sequentially engaging said edges.

22. A surgical instrument according to claim 16 wherein said cartridge member is a rectangular solid member.

23. A surgical instrument according to claim 16 further comprising:
   a plurality of said cartridges member; and
   means to remove one of said cartridges from said housing; and
   means to insert another cartridge into said housing.

24. A surgical instrument according to claim 14 further comprising:
   trigger means for incrementally moving said first cam means relative to said first cam follower means and said second cam means relative to said second cam follower means.

25. A surgical instrument for inserting a cannulated surgical implant into a surgical site, the instrument comprising:
   an elongated needle for slidably receiving said implant thereon, said needle having a proximal end and a distal end;
   an elongated pusher for pushing said implant distally from said needle, said pusher having a proximal end and a distal end;
   first moving means for moving said needle distally a first predetermined distance, said first moving means comprising:
      a first cam means for producing a first predetermined motion of an element associated therewith;
      a first slide member comprising:
         means to engage said needle to enable motion of said first slide member to effect motion of said needle;
         first track means to enable said first slide member to move in a direction aligned with said distal end of said needle; and
         first cam follower means for following said first cam means;
   second moving means for moving said pusher distally a second predetermined distance to thereby slide said implant along said needle, said second moving means comprising:
      a second cam means for producing a second predetermined motion of an element associated therewith;
      a second slide member comprising:
         means to engage said pusher to enable motion of said second slide member to effect motion of said pusher;
         second track means to enable said second slide member to move in a direction aligned with said distal end of said pusher; and
         second cam follower means for following said second cam means.

26. A surgical instrument according to claim 25 further comprising:
   an elongated tube for slidably retaining said implant, said needle and said pusher, said tube having a proximal end and a distal end.

27. A surgical implant assembly selectively attachable to an instrument for inserting a cannulated surgical implant, comprising:
   a cannulated implant;
   an elongated needle for slidably receiving said implant thereon, said needle having a proximal end and a distal end;
   an elongated pusher for pushing said implant distally from said needle, said pusher having a proximal end and a distal end; and
   an elongated tube for slidably retaining said implant, said needle and said pusher, said tube having a proximal end and a distal end.

28. A surgical implant assembly according to claim 27 wherein said surgical implant assembly is for use with elements in a housing and further comprises means at the proximal ends of each of said needle, pusher and tube for engaging same with respective elements in said housing.

29. A surgical system for inserting a selected length cannulated surgical implant into a surgical site, the system comprising:
   a plurality of varying length surgical implant assemblies each comprising an elongated needle for slidably receiving a selected length implant thereon, said needle having a proximal end and a distal end, an elongated pusher for pushing said selected length implant distally from said needle, said pusher having a proximal end and a distal end, an elongated tube for slidably retaining said selected length implant, said needle and said pusher, said tube having a proximal end and a distal end;
   an instrument for receiving a selected one of said plurality of surgical implant assemblies, said instrument comprising:
      a housing;
      first moving means for moving said needle distally a first selected predetermined distance;
      second moving means for moving said pusher distally a second selected predetermined distance to thereby slide said selected implant along said needle and distally from said tube;
      a plurality of interchangeable activating means, each associated with a predetermined one of said selected length implants, each said activating means for controlling motion of said first and second moving means;
      trigger means for moving said activating means; and
      means for interposing a selected one of said activating means between said trigger means and said first and second moving means.

30. A method for implanting a cannulated surgical implant comprising:
   providing within a housing a surgical implant assembly comprising an elongated needle for slidably receiving said implant thereon, said needle having a proximal end and a distal end, an elongated pusher for pushing said implant distally from said needle, said pusher having a proximal end and a distal end, an elongated tube for slidably retaining said implant, said needle and said pusher, said tube having a proximal end and a distal end;
   positioning said implant on said needle and within the distal end of said elongated tube;
   positioning said distal end of said elongated tube at a selected site of implantation;
   providing a trigger means on said housing for cyclical motion to sequentially move said needle and said pusher;
   moving the needle from said elongated tube into the site of implantation;
   moving the pusher from said elongated tube to thereby move said implant along the needle and into the site of implantation; and
   withdrawing said needle from the site of implantation.

31. A method according to claim 30 wherein said moving steps are each accomplished with cyclical user manipulation of said trigger means.

32. A method according to claim 31 wherein said trigger means comprises a single trigger and said moving steps are each accomplished with cyclical user manipulation of said single trigger.

33. A method according to claim 32 wherein said single trigger is cyclically movable between a first position and a second position further comprising the steps of:

moving said single trigger from said first position to said second position to thereby move said needle distally a first predetermined distance;

leaving said needle extended from said tube by said first predetermined distance;

releasing said single trigger to enable it to be restored to said first position;

moving said single trigger from said first position to said second position to thereby move said pusher distally a second predetermined distance to thereby move said implant along said needle and into the site of implantation; and releasing said single trigger to enable it to be restored to said first position.

34. A method according to claim 33 further comprising the steps of:

situating at said proximal end of said needle a needle member having a first predetermined shape;

receiving said needle member in a first receiving chamber; and slidably moving said receiving chamber said first predetermined distance in response to motion of said trigger.

35. A method according to claim 33 further comprising the steps of:

situating at said proximal end of said pusher a pusher member having a second predetermined shape;

receiving said pusher member in a second receiving chamber; and slidably moving said second receiving chamber said second predetermined distance in response to motion of said trigger.

* * * * *